United States Patent
Kopetz et al.

(10) Patent No.: US 12,319,968 B2
(45) Date of Patent: Jun. 3, 2025

(54) GENE MUTATIONS AND COPY NUMBER ALTERATIONS OF EGFR, KRAS AND MET

(71) Applicants: GUARDANT HEALTH, INC., Redwood City, CA (US); BOARD OF REGENTS, THE UNIVERSITY OF TEXAS SYSTEM, Austin, TX (US)

(72) Inventors: Scott Kopetz, Austin, TX (US); AmirAli Talasaz, Atherton, CA (US)

(73) Assignee: Guardant Health, Inc., Palo Alto, CA (US)

(*) Notice: Subject to any disclaimer, the term of this patent is extended or adjusted under 35 U.S.C. 154(b) by 925 days.

(21) Appl. No.: 17/383,390

(22) Filed: Jul. 22, 2021

(65) Prior Publication Data
US 2021/0395836 A1 Dec. 23, 2021

Related U.S. Application Data

(60) Division of application No. 16/291,761, filed on Mar. 4, 2019, now Pat. No. 11,085,086, which is a continuation of application No. 15/348,481, filed on Nov. 10, 2016, now abandoned, which is a continuation of application No. PCT/US2015/030639, filed on May 13, 2015.

(60) Provisional application No. 62/004,749, filed on May 29, 2014, provisional application No. 61/992,877, filed on May 13, 2014.

(51) Int. Cl.
| | | |
|---|---|---|
| C07H 21/04 | (2006.01) | |
| C07K 14/71 | (2006.01) | |
| C07K 14/82 | (2006.01) | |
| C07K 16/28 | (2006.01) | |
| C07K 16/30 | (2006.01) | |
| C12Q 1/68 | (2018.01) | |
| C12Q 1/6886 | (2018.01) | |
| G16B 20/10 | (2019.01) | |
| G16B 20/20 | (2019.01) | |
| G16B 99/00 | (2019.01) | |
| A61K 39/00 | (2006.01) | |

(52) U.S. Cl.
CPC .......... C12Q 1/6886 (2013.01); C07K 14/71 (2013.01); C07K 14/82 (2013.01); C07K 16/2863 (2013.01); C07K 16/30 (2013.01); G16B 20/10 (2019.02); G16B 20/20 (2019.02); G16B 99/00 (2019.02); *A61K 2039/505* (2013.01); *C07K 2317/21* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2008/0293055 A1 | 11/2008 | Freeman et al. |
| 2010/0166744 A1 | 7/2010 | Wong |
| 2013/0143214 A1 | 6/2013 | Schütz et al. |
| 2014/0134158 A1 | 5/2014 | Bardelli et al. |
| 2018/0251848 A1 | 9/2018 | Diehn et al. |
| 2018/0346987 A1* | 12/2018 | Velculescu ........... C12Q 1/6886 |

FOREIGN PATENT DOCUMENTS

| | | |
|---|---|---|
| EP | 2554551 A1 | 2/2013 |
| WO | 2008112274 A2 | 9/2008 |
| WO | 2010145796 A2 | 12/2010 |
| WO | 2011028540 A1 | 3/2011 |
| WO | 2012066451 A1 | 5/2012 |
| WO | 2012131092 A2 | 10/2012 |
| WO | 2013142389 A1 | 9/2013 |
| WO | 2014039556 A1 | 3/2014 |
| WO | 2014182521 A1 | 11/2014 |

OTHER PUBLICATIONS

European Office Action for EP20209515.4, dated Jun. 9, 2023.
International Search Report and Written Opinion for PCT application No. PCT/US2015/030639 datead Nov. 19, 2015.
Arena, S. et al. "Emergence of Multiple EGFR Extracellular Mutations during Cetuximab Treatmentin Colorectal Cancer" Clinical Cancer Research (2015) 21(9):2157-2166.
Buch, I. et al. "Computational Modeling of an Epidermal Growth Factor Receptor Single-Mutation Resistance to Cetuximab in Colorectal Cancer Treatment", Journal of Chemical Information and Modeling, vol. 53, No. 12, Dec. 23, 2013 (Dec. 23, 2013), pp. 3123-3126, XP055418481, US ISSN: 1549-9596, DOI: 10.1021/ci400456m.
Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.
De Rook, et al. "Effects of KRAS, BRAF< NRAS, and PIK3CA mutations on the efficacy of cetuximab plus chemotherapy in chemotherapy-refractory metastatic colorectal cancer: a retrospective consortium analysis" Oncology (2010) 11:753-762.
De Rook, W. et al. KRAS, BRAF, PIK3CA, and PTEN mutations: implications for targeted therapies in metastatic colorectal cancer.
Lynch, T.J. et al. "Activating Mutation sin the Epidermal Growth Factor Receptor Underlying Responsiveness of Non-Small-Cell Lunch Cancer to Gefitinib" NEJM (2004) 350(21):2129-2139.
Misale, S. et al. "Emergence of KRAS mutations and acquired resistance to anti-EGFR therapy in colorectal cancer" Nature (2012) 486:532-535 & Supplemental Information.
Mohan, et al., Changes in colorectal carcinoma genomes under anti-EGFR therapy identified by whole-genome plasma DNA sequencing.,PLoS Genet, doi: 10.1371/journal.pgen.1004271. eCollection 2014.,Mar. 27, 2014, 10(3), e1004271.

(Continued)

Primary Examiner — Jeanine A Goldberg
(74) Attorney, Agent, or Firm — Timothy A. Hott

(57) ABSTRACT

Sequence variants and copy number variations in the EGFR, KRAS and MET genes are biomarkers for resistance to anti-EGFR therapies for cancer. This disclosure provides methods of detecting these biomarkers and using them in the diagnosis and treatment of cancer.

17 Claims, 4 Drawing Sheets

(56) References Cited

OTHER PUBLICATIONS

Molinari, F. et al. "Increased Detection Sensitivity for FRAS Mutations Enhances the prediction of Anti-DGFR Monoclonal Antibody Resistance in Metastatic Colorectal Cancer" Clin Can Res (2011) 17:4901-4914.

Montagut, C. et al. "Identification of a mutation in the extracellular domain of the Epidermal Growth Factor Receptor conferring cetuximab resistance in colorectal cancer", Nature Medicine, vol. 18, No. 2, Jan. 22, 2012 (Jan. 22, 2012), pp. 221-223, XP0551 63287, ISSN: 1078-8956, DOI: 10.1038/nm.2609.

Mouliere, et al. Circulating Cell-Free DNA from Colorectal Cancer Patients May Reveal High KRAS or BRAF Mutation Load Translational Oncology (2013) 6(3):319-328.

Newman, et al. An ultrasensitive method for quantitating circulating tumor DNA with broad patient coverage. Nat Med. May 2014;20(5):548-54. doi: 10.1038/nm.3519. Epub Apr. 6, 2014.

Paez, G.J. et al. "EGFR Mutations in Lung Cancer: Correlation with Clinical Response to Gefitinib Therapy" Science, American Association for the Advancement of Science, vol. 304, Jun. 4, 2004 (Jun. 4, 2004), pp. 1497-1500, XP008136813, ISSN: 0036-8075, DOI: 10.1126/Science.1099314.

Paweletz, C.P. et al. "Bias-corrected targeted next-generation sequencing for rapid, multiplexed detection of actionable alterations in cell-free DNA from advanced lung cancer patients" Clin Canc Res (2016) 22(4):915-922.

Phallen, J. et al. "Direct detection of early-stage cancers using circulating tumor DNA" Sci Trans Med (2017) vol. 9, Issue 403, eaan2415 DOI: 10.1126/scitranslmed.aan2415.

Sharma, S.V. et al. "Epidermal growth factor receptor mutations in lung cancer" Nature Reviews, Cancer, Nature Publishing Group, London, G.B. vol. 7, Mar. 1, 2007 (Mar. 1, 2007), pp. 169-181, XP002556732, ISSN: 1474-175X, DOI: 10.1038/NRC2088.

Spindler, K-L. et al. "Quantitative Cell-Free DNA, KRAS, and BRAF Mutations in Plasma from Patients with Metastatic Colorectal Cancer during Treatment with Cetuximab and Irinotecan" Clin Canc Res (2012) 18:1177-1185.

Strickler, J.H. et al. "Genomic Landscape of Cell-Free DNA in Patients with Colorectal Cancer" Cancer Discovery (2017) 8(2):164-173.

Tan, C-S. et al. "Third generation EGFR TKIs: current data and future directions" Mol Canc (2018) 17:29 (14 pages).

Tan, C-S. et al. "Third generation EGFR TKIs; current data and future directions" Mol Canc (2018) 17:29.

Tougeron, D. et al. "Epidermal growth factor receptor (EGFR) and KRAS mutations during chemotherapy plus anti-EGFR monoclonal antibody treatment in metastatic colorectal cancer" CancChemoPharmacol (2013) 73:397-403.

Yamaoka, T. et al. "Molecular-Targeted Therapies for Epidermal Growth Factor Receptor and Its Resistance Mechanisms" Intl J Mol Sci (2017) 18:2420 (22 pages).

Yang, et al., EGFR gene copy number as a predictive biomarker for the treatment of metastatic colorectal cancer with anti-EGFR monoclonal antibodies: a meta-analysis.,J Hematol Oncol, Aug. 16, 2012,5:52, 1-9.

* cited by examiner

| Time of Gene Analysis | Total N of Patient | EGFR MUT % | EGFR AMPL % | KRAS MUT % | KRAS AMPL % | BRAF MUT % | BRAF AMPL % | MET MUT % | MET AMPL % | SMO MUT % | SMO AMPL % | MYC MUT % | MYC AMPL % |
|---|---|---|---|---|---|---|---|---|---|---|---|---|---|
| Pre-Treat | 56 | None | N/A | None | N/A | 0.01% | N/A | None | N/A | None | N/A | None | N/A |
| Post-Treat | 56 | 18% | 24% | 30% | 6% | 12% | 10% | None | 14% | None | 4% | None | 12% |

| Time of Gene Analysis | Total N of Patient | NRAS MUT % | NRAS AMPL % | ERBB2 MUT % | ERBB2 AMPL % | ALK MUT % | ALK AMPL % | Notch MUT % | Notch AMPL % | PIK3CA MUT % | PIK3CA AMPL % | APC MUT % | APC AMPL % |
|---|---|---|---|---|---|---|---|---|---|---|---|---|---|
| Pre-Treat | 56 | None | N/A | None | N/A | None | N/A | None | N/A | 0.04% | N/A | N/A | N/A |
| Post-Treat | 56 | 4% | None | 6% | None | 7% | None | 18% | 2% | 13% | None | 46% | None |

Figure 2

| Time of Gene Analysis | Total N of Patient | EGFR MUT % | EGFR AMPL | KRAS MUT % | KRAS AMPL | BRAF MUT % | BRAF AMPL | MET MUT % | MET AMPL | SMO MUT % | SMO AMPL | MYC MUT % | MYC AMPL |
|---|---|---|---|---|---|---|---|---|---|---|---|---|---|
| Pre-Treat | 25 | None | N/A | 56% | N/A | None | N/A | None | N/A | None | N/A | None | N/A |
| Post-Treat | 25 | 6% | 19% | 30% | 6% | 19% | 19% | None | 6% | None | 6% | 6% | 13% |

| Time of Gene Analysis | Total N of Patient | NRAS MUT % | NRAS AMPL | ERBB2 MUT % | ERBB2 AMPL | ALK MUT % | ALK AMPL | Notch MUT % | Notch AMPL | PIK3CA MUT % | PIK3CA AMPL | APC MUT % | APC AMPL |
|---|---|---|---|---|---|---|---|---|---|---|---|---|---|
| Pre-Treat | 25 | None | N/A | None | N/A | None | N/A | None | N/A | 0.04% | N/A | N/A | N/A |
| Post-Treat | 25 | 6% | None | None | None | 13% | 13% | 13% | None | 25% | None | 55% | None |

Figure 3

| Patient | EGFR Mutation | EGFR Amplification | KRAS Mutation | KRAS Amplification | MET Amplification |
|---|---|---|---|---|---|
| 1 | WT | X | WT | WT | X |
| 2 | S492R -1.20% | WT | Q61H -0.30% | WT | WT |
| 3 | G465V -0.90% | X | G13D -0.90% | X | WT |
| 4 | WT | X | Q61H -55.60% | WT | X |
| 5 | S492R -0.30% | X | Q61H -0.30% | WT | WT |
| 6 | WT | X | G12C -13.60% | WT | WT |
| 7 | S492R -0.60% D1083N -0.20% | WT | Q61H -0.50% G12R -0.10% | X | X |
| 8 | I491R -7.50% S492R -1.80% K467I -1.80% | X | G12C -0.40% | WT | X |
| 9 | E114D -1.30% | X | WT | WT | WT |
| 10 | K1061T -0.60% | X | WT | WT | WT |
| 11 | WT | WT | Q61H -0.90% | X | X |
| 12 | WT | WT | G13D -46.90% | X | X |
| 13 | T629T -8.20% R251K -7.20% | X | G12C -0.10% | WT | WT |
| 14 | WT | X | G12C -13.60% | WT | WT |

Figure 4

GENE MUTATIONS AND COPY NUMBER ALTERATIONS OF EGFR, KRAS AND MET

CROSS-REFERENCE TO RELATED APPLICATIONS

This application is a divisional application of U.S. patent application Ser. No. 16/291,761, filed Mar. 4, 2019, which is a continuation application of U.S. patent application Ser. No. 15/348,481, filed Nov. 10, 2016, which is a continuation application of International Patent Application No. PCT/US2015/030639, filed May 13, 2015, which claims the benefit of U.S. Provisional Application No. 61/992,877, filed May 13, 2014, and U.S. Provisional Application No. 62/004,749, filed May 29, 2014, each of which is entirely incorporated herein by reference in its entirety.

STATEMENT AS TO FEDERALLY SPONSORED RESEARCH

This invention was made with government support under Contract no. P30 CA016672 awarded by the National Institutes of Health. The government has certain rights in the invention.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND OF THE INVENTION

Cell free DNA ("cfDNA") allows non-invasive assessment of gene mutations, but has not been reported with copy number alterations. Methodologies to integrate mutation and copy number would allow improved insights into mechanisms of resistance and therapeutic opportunities.

SUMMARY OF THE INVENTION

In one aspect, disclosed herein is a method comprising: (a) detecting, in a sample comprising polynucleotides from a subject, at least one EGFR nucleotide sequence variant that encodes an amino acid or codon sequence variant selected from consisting of G465V, T130A, D1083N, I491R, K467I, T211T, K1061T and V876M; and (b) administering to the subject a cancer treatment other than anti-EGFR therapy. In some cases, at least one EGFR nucleotide sequence variant is selected from the group consisting of G>T G465V, A>G T130A, G>A D1083N, T>G I491R, A>T K467I, C>G T211T, A>C K1061T, and G>A V876M. In some cases, the subject has colorectal cancer. In further cases, the subject has colorectal cancer and has been treated with anti-EGFR therapy. In some instances, the detecting comprises detecting a plurality of EGFR nucleotide sequence variants. The detecting may further comprise detecting amplification of an EGFR gene. The administering may comprise administering to the subject a cancer treatment other than cetuximab. In some cases, the sample comprises cell free DNA. In some cases, the sample is a blood sample or a tumor sample. In some examples, the subject has a cancer that is un-responsive to cetuximab. The subject may have a cancer selected from the group consisting of colorectal cancer and head and neck cancer. In some cases, the cancer treatment comprises administering an antibody directed to an epitope of EGFR other than the epitope against which cetuximab is directed. In some cases, the cancer treatment other than anti-EGFR therapy comprises a treatment other than administration of an EGFR-directed antibody. The subject may be refractory to 5-FU-based therapy. The detecting may further comprise DNA sequencing. In some cases, the detecting comprises high-throughput DNA sequencing. In some instances, the detecting comprises sequence capture of polynucleotides containing the at least one EGFR nucleotide sequence variant. In some instances, the detecting is performed with a sensitivity of at least any of 1%, 0.1% or 0.01%. In some instances, the detecting is performed with a specificity of 99%, 99.9% or 99.99%.

In another aspect, a method comprises: (a) monitoring, at one or more times, a subject undergoing anti-EGFR therapy, wherein the monitoring comprises detecting the presence of at least one EGFR nucleotide sequence variant that encodes an amino acid or codon sequence variant selected from the group consisting of G465V, T130A, D1083N, I491R, K467I, T211T, K1061T and V876M; and (b) when the amino acid or codon sequence variant is detected, administering to the subject a cancer treatment other than the anti-EGFR therapy. In some cases, the subject suffers from colorectal cancer. In some cases, the monitoring comprises monitoring the subject at a plurality of different times. In some examples, the presence of at least one EGFR nucleotide sequence variant is monitored in a sample from the subject, wherein the sample comprises cell free DNA. The monitoring may further comprise monitoring the patient to detect amplification of an EGFR gene and, when the amplification of the EGFR gene is detected, administering to the subject a cancer treatment other than the anti-EGFR therapy. The methods may further comprise ceasing the anti-EGFR therapy when the presence of the at least one EGFR nucleotide sequence variant is detected In another aspect, a method is provided comprising: (a) in a sample comprising nucleic acids from a cancer cell of a subject, selectively enriching for one or more nucleic acids comprising EGFR nucleotide sequences, to produce an enriched sample; (b) sequencing the one or more nucleic acids comprising EGFR nucleotide sequences from the enriched sample to produce sequence reads; (c) determining, among the sequence reads, a presence or an absence of at least one EGFR nucleotide sequence variant encoding an amino acid or codon sequence variant selected from the group consisting of G465V, T130A, D1083N, I491R, K467I, T211T, K1061T and V876M; and (d) classifying the subject as having a cancer un-responsive to anti-EGFR therapy. In some cases, the determining comprises determining the presence or the absence of a plurality of EGFR nucleotide sequence variants.

In yet another aspect, a method comprises administering to a subject having a cancer characterized by at least one EGFR nucleotide sequence variant that encodes an amino acid or codon sequence variant selected from the group consisting of G465V, T130A, D1083N, I491R, K467I, T211T, K1061T and V876M, a cancer treatment other than anti-EGFR therapy.

In yet another aspect, a composition is provided comprising one or more solid supports, each of the one or more solid supports having attached thereto a nucleic acid capture probe, wherein each nucleic acid capture probe comprises a nucleotide sequence that hybridizes, under stringent hybridization conditions, to an EGFR nucleotide sequence within 200 nucleotides of a codon encoding an amino acid selected from any of positions: 465, 130, 1083, 491, 467, 211, 1061 and 876. In some cases, the one or more solid supports have attached thereto a plurality of nucleic acid capture probes, each of the plurality of nucleic acid capture probes hybridizing to a different one of the EGFR nucleotide sequences. In some cases, the one or more solid supports comprise magnetically attractable particles.

In yet another aspect, a system is provided comprising a computer readable medium comprising machine-executable code that, upon execution by a computer processor, implements a method comprising: (a) receiving into memory sequence reads of polynucleotides; (b) determining, among the sequence reads, an identity of nucleotides within codons encoding an EGFR amino acid selected from any of positions: 465, 130, 1083, 491, 467, 211, 1061 and 876; (c) reporting a presence of at least one EGFR nucleotide sequence variant encoding an amino acid or codon sequence variant selected from the group consisting of G465V, T130A, D1083N, 1491R, K467I, T211T, K1061T, and V876M, and, optionally, a relative quantity of the nucleotide sequence variant compared with a nucleotide sequence at a same position of a reference human genome.

In yet another aspect, a method is provided comprising: (a) detecting, in a sample comprising polynucleotides from a subject, at least one KRAS mutation and at least one KRAS gene amplification; and (b) administering to the subject a cancer treatment other than anti-EGFR therapy. In some cases, the subject has colorectal cancer. In further cases, the subject has colorectal cancer and has been treated with the anti-EGFR therapy. In some cases, the sample comprises cell free DNA. In some instances, the at least one KRAS mutation is selected from the group consisting of G12C, G12R, G13D and Q61H.

In yet another aspect, a method is provided comprising: (a) monitoring, at one or more times, a subject undergoing anti-EGFR therapy, wherein monitoring comprises detecting the presence of at least one KRAS nucleotide sequence variant and at least one KRAS gene amplification; and (b) when the at least one KRAS nucleotide sequence variant and the at least one KRAS gene amplification are detected, administering to the subject a cancer treatment other than the anti-EGFR therapy. In some cases, the at least one KRAS nucleotide sequence variant is not detected in a primary tumor of the subject or is not detected in a prior test for a presence of a KRAS nucleotide sequence variant in the subject. In some cases, the at least one KRAS nucleotide sequence variant is selected from the group consisting of G12C, G12R, G13D and Q61H.

In yet another aspect, a method is provided comprising: (a) in a sample comprising nucleic acids from a cancer cell of a subject, selectively enriching for one or more nucleic acids comprising KRAS nucleotide sequences, to produce an enriched sample; (b) sequencing the one or more nucleic acids comprising KRAS nucleotide sequences from the enriched sample to produce sequence reads; (c) determining, among the sequence reads, a presence of at least one KRAS nucleotide sequence variant and a presence of at least one KRAS gene amplification; and (d) classifying the subject as having a cancer un-responsive to anti-EGFR therapy. In some cases, the at least one KRAS nucleotide sequence variant is not detected in a primary tumor of the subject or is not detected in a prior test for a presence of a KRAS nucleotide sequence variant in the subject. In some cases, the at least one nucleotide sequence variant is selected from the group consisting of G12C, G12R, G13D and Q61H.

In yet another aspect, a method is provided comprising administering to a subject having a cancer characterized by at least one KRAS nucleotide sequence variant and at least one KRAS gene amplification, a cancer treatment other than anti-EGFR therapy. In some cases, the at least one KRAS nucleotide sequence variant is not detected in a primary tumor of the subject or is not detected in a prior test for a presence of a KRAS nucleotide sequence variant in the subject. In some case, the at least one KRAS nucleotide sequence variant is selected from the group consisting of G12C, G12R, G13D and Q61H.

In yet another aspect, a system is provided comprising a computer readable medium comprising machine-executable code that, upon execution by a computer processor, implements a method comprising: (a) receiving into memory sequence reads of polynucleotides; (b) determining, among said sequence reads, (i) an identity of nucleotide variants of a KRAS gene and (ii) amplification of a KRAS gene; and (c) reporting, a presence of at least one KRAS nucleotide sequence variant and amount of KRAS gene amplification.

In yet another aspect, a method is provided comprising: (a) detecting, in a sample comprising polynucleotides from a subject, at least one KRAS mutation not detected in a primary tumor of the subject; and (b) administering to the subject a cancer treatment other than anti-EGFR therapy. In some cases, the at least one KRAS mutation is selected from the group consisting of G12C, G12R, G13D and Q61H.

In yet another aspect, a method is provided comprising: (a) monitoring, at one or more times, a subject undergoing anti-EGFR therapy, wherein the monitoring comprises detecting a new appearance of at least one KRAS nucleotide sequence variant; and (b) when the at least one KRAS nucleotide sequence variant is detected, administering to the subject a cancer treatment other than the anti-EGFR therapy. In some cases, the at least one KRAS nucleotide sequence variant is selected from the group consisting of G12C, G12R, G13D and Q61H.

In yet another aspect, a method is provided comprising administering to a subject having a cancer characterized by at least one KRAS nucleotide sequence variant not present in a primary tumor, a cancer treatment other than anti-EGFR therapy. In some cases, the at least one KRAS nucleotide sequence variant is selected from the group consisting of G12C, G12R, G13D and Q61H.

In yet another aspect, a method is provided comprising: (a) detecting, in a sample comprising polynucleotides from a subject, a presence of a gene amplification in MET; and (b) when the gene amplification is detected, administering to the subject a cancer treatment other than anti-EGFR therapy. In some cases, the detecting further comprises detecting a presence of a gene amplification in either or both of EGFR and KRAS.

In yet another aspect, a method is provided comprising: (a) detecting, in a sample comprising polynucleotides from a subject, a presence of at least one sequence variant and/or at least one gene amplification in a gene selected from EGFR, KRAS, BRAF, MET, SMO, MYC, NRAS, ERBB2, ALK, Notch, PIK3CA and APC; and (b) when the at least one sequence variant and/or the at least one gene amplification is detected, administering to the subject a cancer treatment other than anti-EGFR therapy. In some cases, the cancer treatment other than anti-EGFR therapy is administered when the at least one sequence variant and/or the at least one gene amplification is detected in at least any of 2, 3, 4, 5, 6, 7, 8, 9, 10, 11 or 12 of the genes. In some cases, the cancer treatment other than anti-EGFR therapy is a therapy effective on a cancer in which such a sequence variant and/or gene amplification is detected.

In yet another aspect, a method is provided comprising: (a) detecting, in a sample comprising polynucleotides from a subject, at least one EGFR nucleotide sequence variant that encodes an amino acid or codon sequence variant selected from the group consisting of G465V, T130A, D1083N, I491R, K467I, T211T, K1061T, and V876M; (b) detecting, in the sample comprising polynucleotides from the subject, a presence of at least one of a KRAS nucleotide sequence variant and a KRAS gene amplification; and (c) administering to the subject a cancer treatment other than anti-EGFR therapy. In some cases, the subject has colorectal cancer. In further cases, the subject has colorectal cancer and has been treated with anti-EGFR therapy. In some cases, step (a) comprises detecting a plurality of EGFR nucleotide sequence variants. In some cases, step (a) further comprises detecting amplification of an EGFR gene. In another case, the at least one KRAS nucleotide sequence variant is a mutation in KRAS. In some cases, the mutation in KRAS is selected from the group consisting of G12C, G12R, G13D and Q61H. In further cases, step (b) comprises detecting at least one KRAS nucleotide sequence variant and at least one KRAS gene amplification. In some cases, the sample comprises cell free DNA.

In yet another aspect, a method is provided comprising: (a) detecting, in a sample comprising polynucleotides from a subject, a gene amplification in at least one of EGFR, BRAF, MYC, and SMO; (b) when the gene amplification in at least one of EGFR, BRAF, MYC, and SMO is detected, administering to the subject a cancer treatment other than anti-EGFR therapy.

BRIEF DESCRIPTION OF THE DRAWINGS

FIG. 2 shows newly detected mutations in KRASwt patients after progression to standard treatment (tumor progressed after cetuximab treatment).

FIG. 3 shows newly detected mutations in KRASmut patients after progression to standard treatment.

FIG. 4 shows concomitant EGFR, KRAS and MET gene alteration.

DETAILED DESCRIPTION OF THE INVENTION

Introduction

Figure 1:
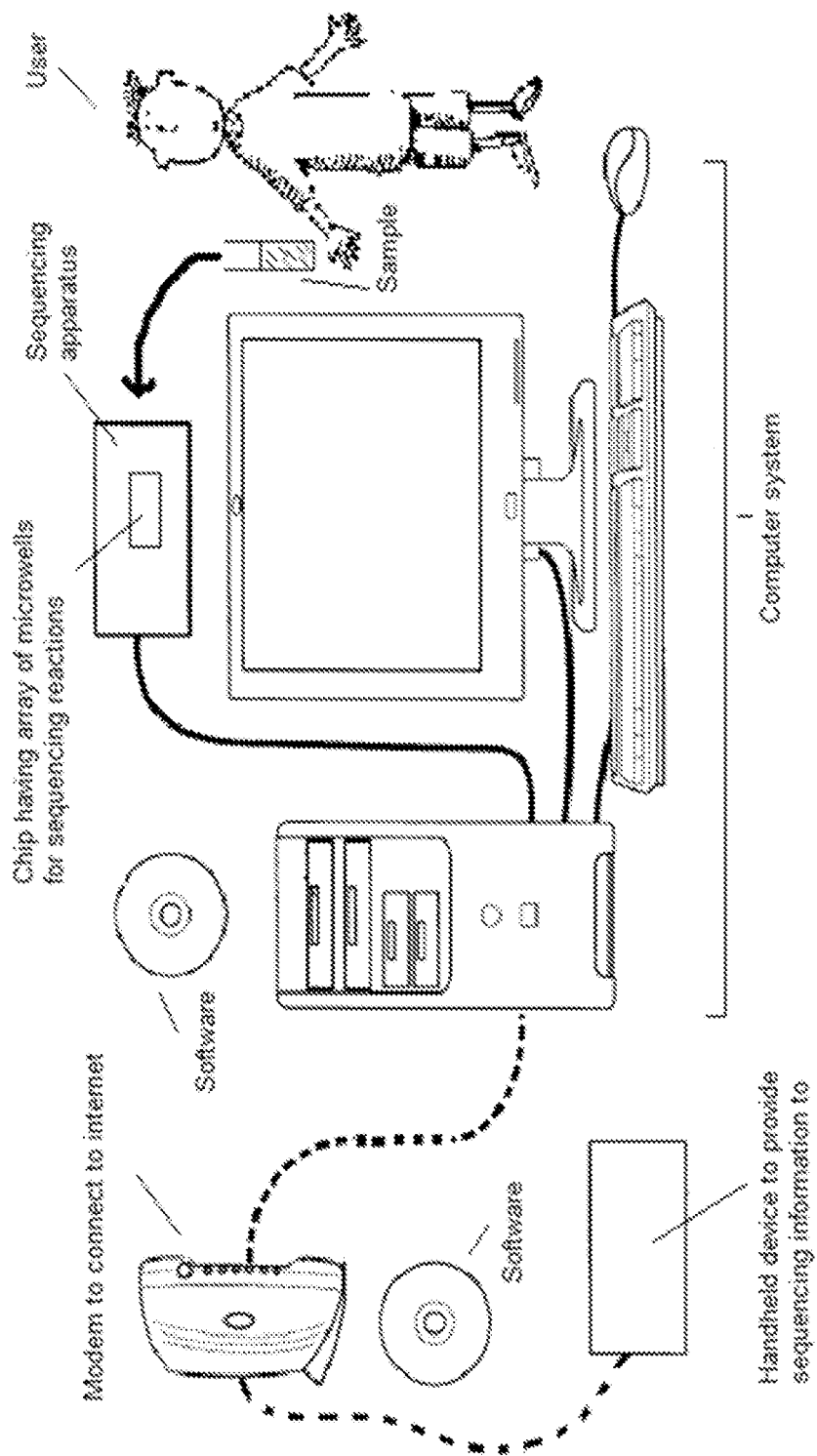
FIG. 1 depicts a schematic representation of a system for analyzing a sample comprising nucleic acids from a user, including a sequencer, bioinformatic software and internet connection for report analysis by, for example, a hand held device or a desk top computer

This disclosure provides methods and compositions for using genetic variants in the diagnosis, prognosis, and treatment selection of a subject, in particular, a subject suffering from cancer. Genetic variants may be nucleotide sequence variations or copy number variations. In particular cases, the methods provide for using genetic variants in the EGFR gene, KRAS gene and MET gene in diagnosis, prognosis, and treatment selection of a subject, in particular, a subject suffering from cancer.

Mutants and amplifications of KRAS and EGFR are correlated with resistance to anti-EGFR therapy in cancer patients, in particular colorectal cancer patients. Detection of these sequence variants and/or gene amplifications can be used to monitor cancer patients and to direct therapy (e.g., as a companion diagnostic).

Methods of the Disclosure

A sample from a subject can be analyzed to detect the presence or the absence of one or more genetic variants, and, if detected, anti-EGFR therapy is reduced or ceased. In other aspects, a sample from a subject is analyzed to detect the presence or the absence of one or more genetic variants, and, if detected, a therapy other than anti-EGFR therapy is commenced. In some cases, the genetic variant is a biomarker.

In one instance, a subject is monitored, at one or more times, for genetic changes indicating the appearance of the biomarker and, when the biomarker is detected, an anti-EGFR therapy is reduced or ceased and/or a therapy other than anti-EGFR therapy is introduced. In particular, the therapy can be one to which a cancer characterized by such a genetic variant is known to respond. Monitoring a subject at one or more times may include, without limitation, monitoring before and after a therapy or surgery, monitoring two or more times before and after a therapy or surgery, and monitoring two or more times after a therapy or surgery. Monitoring may include determining a baseline assessment or baseline status of a subject. Determining a baseline assessment or status of a subject may include determining the presence or absence of a genetic variant in one or more genes prior to treatment with anti-EGFR therapy. The genetic variants may be any one of the genetic variants as listed in Table 1. A baseline assessment may determine that a subject is wild-type or variant for a gene. A subject determined to have a wild-type baseline status may be started on anti-EGFR therapy. A subject determined to have a mutant or variant baseline status may be started on a treatment other than anti-EGFR therapy. Monitoring may further comprise monitoring a subject during or after treatment with anti-EGFR therapy. The subject may be tested for the presence or absence of a genetic variant in a gene. The genetic variant may be any of the genetic variants as listed in Table 1. In one example, a genetic variant may be detected in a gene of a subject during or after anti-EGFR therapy. The genetic variant may be one that was previously undetected in the same subject prior to anti-EGFR therapy. The appearance of a new genetic variant may indicate that the subject is resistant to anti-EGFR therapy. The appearance of a new genetic variant may indicate that the subject be treated with an alternative anti-EGFR therapy or a treatment other than anti-EGFR therapy.

In a particular example, polynucleotides from a subject are selectively enriched for sequences of one or more of the genes as described herein and presence or absence of one or more genetic variants of this disclosure are determined. If detected, the subject is classified as having a cancer unresponsive to anti-EGFR therapy, or having a cancer for which anti-EGFR therapy should be supplemented or replaced with a different anti-EGFR therapy or a therapy other than anti-EGFR therapy. A solid support can be provided that is configured to selectively capture polynucleotides having sequences (e.g., a sequence comprising a genetic alteration, including, specifically, a mutant form associated with anti-EGFR therapy resistance). This support can be used to selectively capture such polynucleotides. Captured polynucleotides can be sequences and sequences can be analyzed for one or more of the biomarkers described herein. Such analysis can be performed by a programmable computer that reports the presence or absence of the one or more genetic variants.

Biomarkers

The disclosure provides methods of using biomarkers for the diagnosis, prognosis, and therapy selection of a subject suffering from e.g., cancer. A biomarker may be any gene or variant of a gene whose presence, mutation, deletion, substitution, copy number, or translation (i.e., to a protein) is an indicator of a disease state. Biomarkers of the present disclosure may include the presence, mutation, deletion, substitution, copy number, or translation in any one or more of EGFR, KRAS, MET, BRAF, MYC, NRAS, ERBB2, ALK, Notch, PIK3CA, APC, and SMO. Biomarkers may be any one of the genetic variants listed in Table 1 below.

TABLE 1

Biomarkers of the disclosure

| Gene | Variant |
|---|---|
| EGFR | G465V |
| EGFR | T130A |
| EGFR | D1083N |
| EGFR | I491R |
| EGFR | K467I |
| EGFR | T211T |
| EGFR | K1061T |
| EGFR | V876M |
| EGFR | S492R |
| EGFR | Gene amplification |
| KRAS | G12C |
| KRAS | G12R |
| KRAS | G13D |
| KRAS | Q61H |
| KRAS | Gene amplification |
| MET | Gene amplification |
| BRAF | Gene amplification |
| SMO | Gene amplification |
| MYC | Gene amplification |
| NRAS | Gene amplification |
| ALK | Gene amplification |
| Notch | Gene amplification |
| PIK3CA | Gene amplification |
| APC | Gene amplification |

EGFR

A biomarker may be a genetic variant detected in the EGFR gene. Nucleotide sequences encoding EGFR can be found at NCBI Reference Sequence NG 007726 (genomic), NCBI Reference Sequence NM_201284.1 (mRNA), NCBI Reference Sequence NM_005228.3 (mRNA), NCBI Reference Sequence NM_201282.1 (mRNA), NCBI Reference Sequence NM_201283.1 (mRNA). Amino acid sequences for EGFR can be found at NCBI Reference Sequence NP_958441.1, NCBI Reference Sequence 958440.1, NCBI Reference Sequence NP_958439.1, and NCBI Accession No. NP_005219.2.

In some cases, the biomarker is a nucleotide sequence variant in EGFR. The nucleotide sequence variant may include, without limitation, G>T G465V, A>G T130A, G>A D1083N, T>G I491R, A>T K467I, C>G T211T, A>C K1061T, A>T K1061T, and G>A V876M. The nucleotide sequence variant may encode an amino acid or codon sequence variant including, without limitation, G465V, T130A, D1083N, I491R, K467I, T211T, K1061T, and V876M corresponding to the amino acid sequences for EGFR as set forth in, e.g., NCBI Accession No. NP_005219.2. In some examples, the nucleotide sequence variant encodes an amino acid or codon sequence variant in the ectodomain of EGFR. Thus, ectodomain mutations may function as biomarkers for anti-EGFR resistance. Examples of such ectodomain mutations may include, without limitation, S492R, G465V, I491R, and K467I. An EGFR nucleotide sequence variant may prevent or reduce the binding of an anti-EGFR antibody to EGFR. The anti-EGFR antibody may be cetuximab. In a particular example, the EGFR variant prevents or reduces binding of cetuximab to EGFR. In such cases, the subject may be treated with an alternative anti-EGFR antibody therapy (e.g., panitumumab) or a treatment other than anti-EGFR therapy. In some cases, a mutation in the EGFR ectodomain may be used to screen for an antibody suitable as an anti-EGFR therapy. In this example, an antibody may be chosen that recognizes an epitope with the particular mutation. In this situation, the antibody may be used as an alternative anti-EGFR therapy to treat subjects that have developed resistance to the primary anti-EGFR therapy.

In some cases, the biomarker is a copy number variation in the EGFR gene. Copy number variation may be an amplification or a deletion or truncation of the EGFR gene. In particular cases, an amplification of the EGFR gene may be detected. An amplification of EGFR may be 3, 4, 5, 6, 7, 8, 9, 10, or 10 or more copies of EGFR. A deletion or truncation of EGFR may be 0 or 1 copies of EGFR. In some cases, an EGFR nucleotide sequence variant and an EGFR gene amplification may be detected.

In some cases, a subject is monitored, at one or more times, for the presence or absence of one or more genetic variants in EGFR. Monitoring a subject at one or more times may include, without limitation, monitoring before and after a therapy or surgery, monitoring two or more times before and after a therapy or surgery, and monitoring two or more times after a therapy or surgery. In some cases, the presence of a genetic variant in EGFR may indicate that the subject is resistant to anti-EGFR therapy. In some cases, the presence of a genetic variant in EGFR may indicate that anti-EGFR therapy is no longer effective to treat a cancer in the subject. In some cases, the presence of the genetic variant is detected in a subject undergoing treatment with anti-EGFR therapy. In some cases, the genetic variant is undetectable in the primary tumor of the subject. In some cases, the genetic variant is undetectable in a prior test for the presence of the EGFR genetic variant. If a genetic variant is detected, the anti-EGFR therapy may be reduced or ceased and an alternative therapy may be commenced. The alternative therapy may be an alternative anti-EGFR therapy or a therapy other than anti-EGFR therapy.

KRAS

A biomarker may be a genetic variant detected in the KRAS gene. Nucleotide sequences encoding KRAS can be found at NCBI Reference Sequence NG 007524.1 (genomic), NCBI Reference Sequence NM_033360.3 (mRNA), NCBI Reference Sequence XM_006719069.1 (mRNA), and NCBI Reference Sequence NM_004985.4 (mRNA). Amino acid sequences for KRAS can be found at NCBI Reference Sequence XP_006719132.1, NCBI Reference Sequence NP_203524.1, and NCBI Reference Sequence NP_004976.2.

In some cases, a biomarker is a nucleotide sequence variant in KRAS. The KRAS nucleotide sequence variant may encode an amino acid or codon sequence variant including, without limitation, G12C, G12R, G13D and Q61H corresponding to the amino acid sequence as set forth in, for example, NCBI Reference Sequence NP_004976.2. In some cases, the genetic variant is a copy number variation in KRAS. The copy number variation can be a gene amplification or deletion. In particular cases, an amplification of the KRAS gene may be detected. An amplification of KRAS may be 3, 4, 5, 6, 7, 8, 9, 10, or 10 or more copies of KRAS. A deletion or truncation of KRAS may be 0 or 1 copies of KRAS. In some cases, a KRAS nucleotide sequence variant and a KRAS gene amplification may be detected.

In some cases, a subject is monitored, at one or more times, for the presence or absence of one or more genetic variants in KRAS. Monitoring a subject at one or more times may include, without limitation, monitoring before and after a therapy or surgery, monitoring two or more times before and after a therapy or surgery, and monitoring two or more times after a therapy or surgery. In some cases, the presence of a genetic variant in KRAS may indicate that the subject is resistant to anti-EGFR therapy. In some cases, the presence of a genetic variant in KRAS may indicate that anti-EGFR therapy is no longer effective to treat a cancer in the subject. In some cases, the presence of the genetic variant is detected in a subject undergoing treatment with anti-EGFR therapy. In some cases, the genetic variant is undetectable in the primary tumor of the subject. In some cases, the genetic variant is undetectable in a prior test for the presence of the KRAS genetic variant. If a genetic variant is detected, the anti-EGFR therapy may be reduced or ceased and an alternative therapy may be commenced. The alternative therapy may be an alternative anti-EGFR therapy or a therapy other than anti-EGFR therapy.

MET

A biomarker may be a genetic variant detected in the MET gene. Nucleotide sequences encoding MET can be found at NCBI Reference Sequence NG_008996.1 (genomic), NCBI Reference Sequence XM_006715991.1 (mRNA), NCBI Reference Sequence XM_006715990.1 (mRNA), NCBI Reference Sequence XM_006715989.1 (mRNA), NCBI Reference SequenceXM_006715988.1 (mRNA), NCBI Reference NM_001127500.1 (mRNA), and NCBI Reference Sequence NM_000245.2 (mRNA). Amino acid sequences for MET can be found at NCBI Reference Sequence XP_006716054.1, NCBI Reference Sequence XP_006716053.1, NCBI Reference Sequence XP_006716052.1, NCBI Reference Sequence XP_006716051.1, NCBI Reference Sequence NP_001120972.1, and NCBI Reference Sequence NP_000236.2.

A genetic variant can be a copy number variation in MET. The copy number variation can be a gene amplification or a truncation. In particular cases, a sample derived from a subject is analyzed for an amplification of the MET gene. An amplification of MET may be 3, 4, 5, 6, 7, 8, 9, 10, or 10 or more copies of MET. A deletion or truncation of MET may be 0 or 1 copies of MET. In some cases, an amplification of the MET gene is detected with an amplification in at least one of EGFR and KRAS. The subject is preferably on anti-EGFR therapy, or is in need thereof.

In some cases, the subject is monitored, at one or more times, for the presence or absence of one or more genetic variants in MET. Monitoring a subject at one or more times may include, without limitation, monitoring before and after a therapy or surgery, monitoring two or more times before and after a therapy or surgery, and monitoring two or more times after a therapy or surgery. In some cases, the presence of a genetic variant in MET may indicate that the subject is resistant to anti-EGFR therapy. In some cases, the presence of a genetic variant in MET along with an amplification in at least one of EGFR and KRAS may indicate that the subject is resistant to anti-EGFR therapy. In particular, copy number variations in any two, or all three of EGFR, KRAS and MET may be indicative of anti-EGFR therapy resistance. In some cases, the presence of the genetic variant(s) is/are detected in a subject undergoing treatment with anti-EGFR therapy. In some cases, the genetic variant(s) is/are undetectable in the primary tumor of the subject. In some cases, the genetic variant(s) is/are undetectable in a prior test for the presence of the same genetic variants. In these examples, the anti-EGFR therapy may be reduced or ceased and an alternative therapy may be commenced. The alternative therapy may be an alternative anti-EGFR therapy or a therapy other than anti-EGFR therapy.

Other Genes

A subject resistant to anti-EGFR therapies may exhibit sequence variants and/or copy number variations in at least one of a plurality of different genes. These include, without limitation, sequence variations in the EGFR, KRAS, BRAF, MYC, NRAS, ERBB2, ALK, Notch, PIK3CA and APC genes; and copy number variations in the EGFR, KRAS, BRAF, MET, SMO, MYC, ALK and Notch genes.

In some cases, the subject is monitored, at one or more times, for the presence or absence of one or more genetic variants in any one of these genes. In some cases, the presence of a genetic variant in any one of EGFR, KRAS, MET, BRAF, MYC, NRAS, ERBB2, ALK, Notch, PIK3CA, SMO, and APC genes may indicate that the subject is resistant to anti-EGFR therapy. In some cases, the presence of a genetic variant in any one of these genes along with an amplification in at least one of EGFR and KRAS may indicate that the subject is resistant to anti-EGFR therapy. In some cases, the presence of a genetic variant in any one of these genes may indicate that anti-EGFR therapy is no longer effective to treat a cancer in the subject. In some cases, the presence of a genetic variant in any one of these genes along with an amplification in at least one of EGFR and KRAS may indicate that anti-EGFR therapy is no longer effective to treat a cancer in the subject. In some cases, the presence of the genetic variant(s) is/are detected in a subject undergoing treatment with anti-EGFR therapy. In some cases, the genetic variant(s) is/are undetectable in the primary tumor of the subject. In some cases, the genetic variant(s) is/are undetectable in a prior test for the presence of the same genetic variants. In these examples, the anti-EGFR therapy may be reduced or ceased and an alternative therapy may be commenced. The alternative therapy may be an alternative anti-EGFR therapy or a therapy other than anti-EGFR therapy.

Anti-EGFR Therapy

Anti-EGFR therapy may refer to any therapy directed at blocking the expression or activity of EGFR, e.g., directly or through its pathway. In certain embodiments, EGFR-therapy involves the use of antibodies, e.g., monoclonal antibodies, directed against EGFR. Non-limiting examples of antibodies suitable for use as anti-EGFR therapy include cetuximab (Trade Name: Erbitux) and panitumumab (Trade Name: Vectibex). In some cases, anti-EGFR therapy may involve the use of EGFR tyrosine kinase inhibitors. Non-limiting examples of EGFR tyrosine kinase inhibitors include gefitinib (Trade Name: Iressa), erlotinib (Trade Name: Tarceva), lapatinib, and canertinib. In particular cases, the anti-EGFR therapy is cetuximab. In some instances, anti-EGFR therapy may be used in combination with a therapy other than anti-EGFR therapy. Anti-EGFR therapy may be used in combination with any combination of chemotherapeutic agents or chemotherapeutic regimens, for example, FOLFOX (fluorouracil [5-FU]/leucovorin/oxaliplatin), FOLFIRI (5-FU/leucovorin/irinotecan), and the like.

Cancer Treatments Other than Anti-EGFR Therapy

In some aspects, a cancer treatment other than anti-EGFR therapy may be administered to a subject. In some cases, the cancer treatment other than anti-EGFR therapy is administered in combination with anti-EGFR therapy. In some cases, the cancer treatment other than anti-EGFR therapy is an antibody that is directed to an epitope of EGFR other than the epitope against which cetuximab is directed. In some cases, the cancer treatment other than anti-EGFR therapy includes, without limitation, imatinib, gefatinib, afatinib, dacomitinib, sunitinib, sorafenib, vandetanib, brivanib, cabozantib, neratinib, tivantinib, bevacizumab, cixutumumab, dalotuzumab, figitumumab, rilotumumab, onartuzumab, ganitumab, ramucirumab, ridaforolimus, tensirolimus, everolimus, BMS-690514, BMS-754807, EMD 525797, GDC-0973, GDC-0941, MK-2206, AZD6244, GSK1120212, PX-866, XL821, IMC-A12, MM-121, PF-02341066, RG7160, and Sym004.

Cancers

Anti-EGFR therapies may be used in the treatment of various cancers, including metastatic colorectal cancer, metastatic non-small cell lung cancer and head and neck cancer. However, these cancers can eventually become resistant to anti-EGFR therapies. Subjects and cancer patients that can benefit from the methods of this disclosure include those suspected of having cancer, those having cancer for whom no treatment has begun, those in the course of treatment that are not resistant to anti-EGFR therapies, and those resistant to anti-EGFR therapies.

Biological Samples

The disclosure provides for detecting genetic variations in biological samples from a subject. Biological samples may include polynucleotides from cancer cells. Polynucleotides may be DNA (e.g., genomic DNA, cDNA), RNA (e.g., mRNA, small RNAs), or any combination thereof. Biological samples may include tumor tissue, e.g., from a biopsy. In some cases, biological samples may include blood or saliva. In particular cases, biological samples may comprise cell free DNA ("cfDNA"). Cell free DNA can be present in, e.g., blood.

Genetic Analysis

Genetic analysis includes detection of nucleotide sequence variants and copy number variations. Genetic variants can be determined by sequencing. The sequencing method can be massively parallel sequencing, that is, simultaneously (or in rapid succession) sequencing any of at least 100,000, 1 million, 10 million, 100 million, or 1 billion polynucleotide molecules. Sequencing methods may include, but are not limited to: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next-generation sequencing, Single Molecule Sequencing by Synthesis (SMSS)(Helicos), massively-parallel sequencing, Clonal Single Molecule Array (Solexa), shotgun sequencing, Maxam-Gilbert or Sanger sequencing, primer walking, sequencing using PacBio, SOLiD, Ion Torrent, or Nanopore platforms and any other sequencing methods known in the art.

Sequencing can be made more efficient by performing sequence capture, that is, the enrichment of a sample for target sequences of interest, e.g., sequences including the KRAS and/or EGFR genes or portions of them containing sequence variant biomarkers. Sequence capture can be performed using immobilized probes that hybridize to the targets of interest.

Cell free DNA can include small amounts of tumor DNA mixed with germline DNA. Sequencing methods that increase sensitivity and specificity of detecting tumor DNA, and, in particular, genetic sequence variants and copy number variation, can be useful in the methods of this invention. Such methods are described in, for example, in WO 2014/039556. These methods not only can detect molecules with a sensitivity of up to or greater than 0.1%, but also can distinguish these signals from noise typical in current sequencing methods. Increases in sensitivity and specificity from blood-based samples of cfDNA can be achieved using various methods. One method includes high efficiency tagging of DNA molecules in the sample, e.g., tagging at least any of 50%, 75% or 90% of the polynucleotides in a sample. This increases the likelihood that a low-abundance target molecule in a sample will be tagged and subsequently sequenced, and significantly increases sensitivity of detection of target molecules.

Another method involves molecular tracking, which identifies sequence reads that have been redundantly generated from an original parent molecule, and assigns the most likely identity of a base at each locus or position in the parent molecule. This significantly increases specificity of detection by reducing noise generated by amplification and sequencing errors, which reduces frequency of false positives.

Methods of the present disclosure can be used to detect genetic variation in non-uniquely tagged initial starting genetic material (e.g., rare DNA) at a concentration that is less than 5%, 1%, 0.5%, 0.1%, 0.05%, or 0.01%, at a specificity of at least 99%, 99.9%, 99.99%, 99.999%, 99.9999%, or 99.99999%. Sequence reads of tagged polynucleotides can be subsequently tracked to generate consensus sequences for polynucleotides with an error rate of no more than 2%, 1%, 0.1%, or 0.01%.

Copy number variation determination can involve determining a quantitative measure of polynucleotides in a sample mapping to a genetic locus, such as the EGFR gene or KRAS gene. The quantitative measure can be a number. Once the total number of polynucleotides mapping to a locus is determined, this number can be used in standard methods of determining Copy Number Variation at the locus. A quantitative measure can be normalized against a standard. In one method, a quantitative measure at a test locus can be standardized against a quantitative measure of polynucleotides mapping to a control locus in the genome, such as gene of known copy number. In another method, the quantitative measure can be compared against the amount of nucleic acid in the original sample. For example, the quantitative measure can be compared against an expected measure for diploidy. In another method, the quantitative measure can be normalized against a measure from a control sample, and normalized measures at different loci can be compared. In another method, quantifying involves quantifying parent or original molecules in a sample mapping to a locus, rather than number of sequence reads. A copy number variation may be an amplification or a deletion or truncation of a gene. An amplification may be 3, 4, 5, 6, 7, 8, 9, 10, or 10 or more copies of a gene. A deletion or truncation may be 0 or 1 copies of a gene.

An example of a method for detecting copy number variation may include an array. The array may comprise a plurality of capture probes. The capture probes can be oligonucleotides that are bound to the surface of the array. The capture probes may hybridize to at least one of the genes as set forth in Table 1. The capture probes may bind to at least 1, 2, 3, 4, 5, 6, 7, 8, 9, 10, 11, or 12 genes as set forth in Table 1. DNA derived from the subject may be labeled (e.g., with a fluorophore) prior to hybridization for detection.

In other examples, a gene of interest may be amplified using primers that recognize the gene of interest. The primers may hybridize to a gene upstream and/or downstream of a particular region of interest (e.g., upstream of a mutation site). A detection probe may be hybridized to the amplification product. Detection probes may specifically hybridize to a wild-type sequence or to a mutated/variant sequence. Detection probes may be labeled with a detectable label (e.g., with a fluorophore). Detection of a wild-type or mutant sequence may be performed by detecting the detectable label (e.g., fluorescence imaging). In examples of copy number variation, a gene of interest may be compared with a reference gene. Differences in copy number between the gene of interest and the reference gene may indicate amplification or deletion/truncation of a gene. Examples of platforms suitable to perform the methods described herein include digital PCR platforms such as e.g., Fluidigm Digital Array.

Diagnostic Methods

Biomarkers of this invention, i.e., sequence variants and/or copy number variants, can be used in diagnostic methods. In one method, the biomarker is detected in a sample and then correlated to a condition, e.g., resistance to anti-EGFR therapy. In another method, the presence of the biomarker is used to stratify treatment options. For example, if a person has a biomarker of this disclosure, anti-EGFR therapies can be ranked below other therapies, such as dual kinase inhibition of EGFR and HR2, Bevacizumab-containing regimens, or best supportive care. In another method, detection of these biomarkers in a subject can be followed by initiating an alternative therapy, such as a non-anti-EGFR therapy or a different EGFR therapy in addition to or in place of an anti-EGFR therapy. In another method, detecting the biomarkers of this disclosure is used to make a prognosis for a subject. For example, detecting the biomarkers can be correlated with a shortened life expectancy. In another method, a patient undergoing treatment for a cancer responsive to anti-EGFR therapy is monitored for the biomarkers of this disclosure. Appearance of the biomarkers can indicate that anti-EGFR therapies can or are failing, and direct a physician to initiate a different therapy regimen.

Compositions

In some aspects, the disclosure provides for compositions suitable for performing the methods described herein. In some cases, the composition may be used to selectively enrich for one or more nucleic acids comprising any of the genes described herein. In some cases, the composition comprises one or more solid supports. The one or more solid supports may be a magnetically attractable particle (i.e., a magnetic bead). The solid support can comprise a plurality of capture probes (e.g., oligonucleotides specifically hybridizing to certain sequences). For example, the probes can hybridize within certain genomic regions, e.g., genes. In some cases, the genomic regions, e.g., genes, can be regions associated with diseases, e.g., cancer. After enrichment, the selected fragmented can be attached to any sequencing adaptor suitable for use on any sequencing platform disclosed herein. For example, a sequence adaptor can comprise a flow cell sequence, a sample barcode, or both. In another example, a sequence adaptor can be a hairpin shaped adaptor and/or comprise a sample barcode. Further, the resulting fragments can be amplified and sequenced. In some cases, the adaptor does not comprise a sequencing primer region.

In some examples, the solid support may be an array. The array may comprise a plurality of capture probes. The capture probes can be oligonucleotides that are bound to the surface of the array. The capture probes may selectively hybridize to a sequence of interest. The sequence of interest may be a wild-type sequence or a mutant/variant sequence. The wild-type and mutant/variant sequences may represent any gene or any genetic variant as set forth in Table 1. The capture probes may bind to at least 1, 2, 3, 4, 5, 6, 7, 8, 9, 10, 11, or 12 genes as set forth in Table 1.

In a particular case, one or more solid supports comprising a nucleic acid capture probe attached thereto can be used to selectively enrich one or more nucleic acids comprising an EGFR nucleotide sequence. In this example, the capture probe may comprise a nucleotide sequence that hybridizes, under stringent hybridization conditions, to an EGFR nucleotide sequence. In some cases, the capture probes can hybridize to the EGFR nucleotide sequence within 200 nucleotides of a codon encoding an amino acid selected from any of positions, without limitation: 465, 130, 1083, 491, 467, 211, 1061 and 876. Amino acid sequences for EGFR are as set forth in e.g., NCBI Accession No. NP_005219.2. In some cases, a plurality of capture probes, each hybridizing to a different one of the EGFR nucleotide sequences, are attached to the one or more solid supports. In some cases, the composition comprises reagents for preferentially enriching for molecules with the nucleotide variation from molecules without the nucleotide variation.

Systems

Sequence data can be analyzed by computer to identify sequence variants among sequence reads and/or to make quantitative measures of sequences of interest, e.g., for determination of copy number variation. FIG. 1 schematically illustrates a system for analyzing a sample comprising nucleic acids from a subject. The system includes a sequencer, bioinformatic software and an internet connection for report analysis by, for example, a hand held device or a desktop computer.

In one aspect, a system is provided comprising a computer readable medium comprising machine-executable code that, upon execution by a computer processor, implements a method of the present disclosure. The computer processor may be particularly tailored to implement methods provided herein, such as with the aid of software having one or more algorithms that are directed to implementing such methods. The system may receive into memory sequence reads of polynucleotides. Sequence reads may be generated by any sequencing platform disclosed herein. The system may then determine an identity of nucleotides from the sequencing reads. The system then may report a presence of at least one nucleotide sequence variant present in a gene as disclosed herein. In some cases, the system may optionally report a relative amount of the nucleotide sequence variant compared with a nucleotide sequence at a same position of a reference human genome. The report may indicate a subject as having a cancer un-responsive to anti-EGFR therapy. The report may indicate that anti-EGFR therapy should be ceased or reduced. The report may further indicate that an alternative EGFR therapy or a treatment other than anti-EGFR therapy should commence. The report may be directly provided to the subject or may be provided to the healthcare provider.

In a particular example, the system may determine an identity of nucleotides that encode an amino acid from the EGFR gene at any of positions 465, 130, 1083, 491, 467, 211, 1061, and 876. The system may further report a presence of at least one EGFR nucleotide sequence variant encoding an amino acid or codon sequence variant selected from the group consisting of G465V, T130A, D1083N, I491R, K467I, T211T, K1061T, and V876M.

In other examples, the system may determine an identity of nucleotide variants of a KRAS gene and amplification of the KRAS gene. The system may further report, from the sequence reads, a presence of at least one KRAS nucleotide sequence variant and an amount of KRAS gene amplification. The report may indicate that the subject be treated with a therapy other than anti-EGFR therapy.

Kits

In some aspects, the disclosure provides kits suitable for performing the methods described herein. In some cases, the kit may include materials for the collection of a biological sample. These materials may include, without limitation, a device for collecting a biological sample, for example, a needle and syringe for collection of a blood sample or a swab for collection of a saliva sample from a subject. Alternatively, a subject may spit into a tube. The kit may further include a container for collecting the biological sample, an alcohol wipe for disinfecting the skin, instructions for collecting the biological sample, and the like.

In some cases, the kit may include a plurality of oligonucleotide probes that selectively hybridize to at least 1, 2, 3, 4, 5, 6, 7, 8, 9, 10, 11, or 12 genes selected from the group consisting of EGFR, KRAS, BRAF, MET, SMO, MYC, NRAS, ERBB2, ALK, Notch, PIK3CA, APC. The oligonucleotide probes may be capture probes. The capture probes may be bound to the surface of a solid support. The solid support may be a magnetically attractable particle. The kit can include a container that includes the plurality of oligonucleotide probes and instructions for performing any of the methods described herein.

In some cases, the kits may further include any component suitable for use with the genetic analysis methods disclosed herein. Non-limiting examples of these components include molecular barcodes or tags, sequencing adaptors suitable for use in e.g., Illumina sequencing, reagents for amplification of target-enriched sequences, and the like.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Identification of Genetic Variants Correlated with Resistance to Anti-EGFR Therapy Genetic alterations are a common feature of colorectal cancer (CRC), and some of them have been identified as predictive biomarkers for treatment selections. Applying methodologies to evaluate tumor genetic changes into clinical routine is a strategic tool to improve patient screening and treatment selection. Cell free DNA (cfDNA) provides an adequate source of tumor genetic material to monitor patient tumor genetic evolution under treatment pressure. Cell free DNA (cfDNA) extracted from metastatic CRC patient plasma samples were used to detect new mutations after standard care treatment progression.

Methods: cfDNA extracted from metastatic CRC patient (pt) plasma samples were analyzed by sequencing technology from Guardant Health, Inc. for mutations and amplification of 54 genes as set forth in Table 2. An assessment was performed on the subjects, prior to treatment, to determine the baseline status of these genes (i.e., wild-type or mutant/variant). Treatment was selected based on the baseline status (e.g., a wild-type baseline indicated that the subject should be treated with anti-EGFR therapy, whereas a mutant/variant status indicated a patient should be treated with a treatment other than anti-EGFR therapy). Patients were monitored during treatment using a next-generation sequencing (NGS)-based assay to identify potential tumor-related genomic alterations as mutations and gene copy numbers. The lower limit of detection was 0.1% mutant alleles in a wild-type background. All patients were enrolled in the ATTACC program for mCRC patients who progressed on standard treatment, and had sequencing of the primary tumor performed for a 46-gene panel.

TABLE 2

54 Gene Panel for Assessing Baseline Status of a Patient

| Gene | Protein |
| --- | --- |
| ALK | ALK tyrosine kinase receptor |
| APC | Adenomatous polyposis coli protein |
| AR | Androgen receptor |
| BRAF | Serine/threonine-protein kinase B-raf |
| CDKN2A | Cyclin-dependent kinase inhibitor 2A |
| EGFR | Epidermal growth factor receptor |
| ERBB2 | Receptor tyrosine-protein kinase erbB-2 |
| FBW7 | F-box/WD repeat-containing protein 7 |
| KRAS | GTPase KRas |
| MET | Hepatocyte growth factor receptor |
| MYC | Myc proto-oncogene protein |
| NOTCH1 | Neurogenic locus notch homolog protein 1 |
| NRAS | GTPase NRas |
| PIK3CA | Phosphatidylinositol 4,5-bisphosphate 3-kinase catalytic subunit alpha isoform |
| PTEN | Phosphatidylinositol 3,4,5-trisphosphate 3-phosphatase and dual-specificity protein phosphatase |
| PROC | Vitamin K-dependent protein C |
| RB1 | Retinoblastoma-associated protein |
| TP53 | Cellular tumor antigen p53 |
| ABL1 | Tyrosine-protein kinase ABL1 |
| AKT1 | RAC-alpha serine/threonine-protein kinase |
| ATM | Serine-protein kinase ATM |
| CDH1 | Cadherin-1 |
| CSF1R | Macrophage colony-stimulating factor 1 receptor |
| CTNNB1 | Catenin beta-1 |
| ERBB4 | Receptor tyrosine-protein kinase erbB-4 |
| EZH2 | Histone-lysine N-methyltransferase EZH2 |
| FGFR1 | Fibroblast growth factor receptor 1 |
| FGFR2 | Fibroblast growth factor receptor 2 |
| FGFR3 | Fibroblast growth factor receptor 3 |
| FLT3 | Receptor-type tyrosine-protein kinase FLT3 |
| GNA11 | Guanine nucleotide-binding protein subunit alpha-11 |
| GNAQ | Guanine nucleotide-binding protein G(q) subunit alpha |
| GNAS | Guanine nucleotide-binding protein G(s) subunit alpha |
| HNF1A | Hepatocyte nuclear factor 1-alpha |
| HRAS | GTPase HRas |
| IDH1 | Isocitrate dehydrogenase [NADP], cytoplasmic |
| IDH2 | Isocitrate dehydrogenase [NADP], mitochondrial |
| JAK2 | Tyrosine-protein kinase JAK2 |
| JAK3 | Tyrosine-protein kinase JAK3 |
| KDR | Vascular endothelial growth factor receptor 2 |
| KIT | Mast/stem cell growth factor receptor Kit |
| MLH1 | DNA mismatch repair protein Mlh1 |
| MPL | Thrombopoietin receptor |
| NPM1 | Nucleophosmin |
| PDGFRA | Platelet-derived growth factor receptor alpha |
| PTPN11 | Tyrosine-protein phosphatase non-receptor type 11 |
| RET | Proto-oncogenic tyrosine-protein kinase receptor Ret |
| SMAD4 | Mothers against decapentaplegic homolog 4 |
| SMARCB1 | SWI/SNF-related matrix-associated actin-dependent regulator of chromatin subfamily B member 1 |
| SMO | Smoothened homolog |
| SRC | Proto-oncogene tyrosine-protein kinase Src |

TABLE 2-continued

54 Gene Panel for Assessing Baseline Status of a Patient

| Gene | Protein |
| --- | --- |
| STK11 | Serine/threonine-protein kinase STK11 |
| TERT | Telomerase reverse transcriptase |
| VHL | Von Hippel-Lindau disease tumor suppressor |

Sample Characteristics:
- 71 Plasma Samples from stage IV CRC enrolled in the ATTACC program at the MDACC were analyzed.
- 56 were KRASwt and BRAFwt status at the baseline assessment and 49/56 received and progressed to standard treatment and to anti-EGFR treatment.
- 25 were KRASmut and/or BRAFmut and received and progressed to standard of care chemotherapy not including anti-EGFR treatment.
- Patients had primary tumor sequencing performed for 46-gene panel.

Results: 71 pt plasma samples were analyzed. All pts were refractory to 5-FU-based therapy, with 49 pts previously treated with anti-EGFR monoclonal antibodies (mAbs).

In patients treated with EGFR mAbs, 30% of pts (n=15) had detection of KRAS mutations not detectable in the primary tumor, compared to 5% (n=1) of pts without EGFR mAb treatment (odds ratio 8.6, P=0.027). (FIG. 2) In 6 of the 15 cases, newly detectable KRAS mutations were associated with KRAS gene amplification, compared to 0 of 16 cases with KRAS mutations detected in the primary tumor (P=0.007). (FIG. 3)

7 ectodomain mutations in EGFR that may alter binding affinity of EGFR mAbs were detected in EGFR mAb treated patients, including S492R (n=4) and three previously unreported mutations G465V, I491R, K467I; concurrent EGFR amplifications were present in 6 of the 7 cases.

14% of EGFR mAbs treated patients developed detectable MET amplifications, which co-existed with KRAS or EGFR mutations in 4 of the 7 cases.

Amplifications in EGFR, BRAF, MYC, and SMO were detected in the plasma in 23%, 11%, 11%, and 4% of subjects resistant to anti-EGFR therapy, respectively, representing rates higher than reported in untreated primary tumors.

Conclusions: Advances in sequencing and bioinformatics allow detection of copy number alternations from cfDNA in plasma. Copy number alterations in treatment refractory mCRC are more common than previously described, and frequently co-exist with mutations after EGFR mAb treatment.

Example 2. Protocol for Treating a Patient with a Therapy Other than Anti-EGFR Therapy A patient presents at the hospital with metastatic colorectal cancer (mCRC). Cell free DNA is collected from the patient to determine a baseline assessment of EGFR, KRAS, and MET status. The patient is determined to be wildtype at the KRAS and MET genes. The patient undergoes anti-EGFR therapy (e.g., cetuximab). The patient is monitored every six months to determine any changes in EGFR, KRAS, and MET status. After two years on anti-EGFR therapy, a mutation previously undetected in EGFR (e.g., G465V) and an amplification in KRAS (e.g., 8 copies as compared to 2 copies) are detected. Cetuximab treatment is ceased and the patient is started on a therapy other than anti-EGFR therapy.

Example 3. Protocol for First Time Therapy Selection

A patient presents at the hospital with metastatic colorectal cancer (mCRC). Cell free DNA is collected from the patient to determine a baseline assessment of EGFR, KRAS, and MET status. The patient is determined to have a gene amplification and a nucleotide sequence variation in KRAS (e.g., G13D) indicating resistance to EGFR therapy. The patient is treated with standard of care chemotherapy not including anti-EGFR therapy.

Example 4. Protocol for Treating a Patient with an Alternative Anti-EGFR Therapy A patient presents at the hospital with metastatic colorectal cancer (mCRC). Cell free DNA is collected from the patient to determine a baseline assessment of EGFR, KRAS, and MET status. The patient is determined to be wildtype at the KRAS and MET genes. The patient undergoes anti-EGFR therapy with cetuximab. The patient is monitored every six months to determine any changes in EGFR, KRAS, and MET status. After two years on anti-EGFR therapy, a mutation previously undetected in EGFR (e.g., G465V) and an amplification in KRAS (e.g., 8 copies as compared to 2 copies) are detected. Cetuximab treatment is ceased and the patient is started on an alternative anti-EGFR antibody therapy (e.g., panitumumab).

Example 5. Protocol for Treating a Patient with a Therapy Other than Anti-EGFR Therapy A patient presents at the hospital with metastatic colorectal cancer (mCRC). Cell free DNA is collected from the patient to determine a baseline assessment of EGFR, KRAS, MET, BRAF, ERBB2, MYC, NRAS, ALK, Notch, PIK3CA, SMO and APC status. The patient is determined to be wildtype at the KRAS, MET, BRAF, ERBB2, MYC, NRAS, ALK, Notch, PIK3CA, SMO and APC genes indicating that the patient is a candidate for anti-EGFR therapy. The patient undergoes anti-EGFR therapy (e.g., cetuximab). The patient is monitored every six months to determine any changes in gene status. After two years on anti-EGFR therapy, a gene amplification in BRAF (e.g., 12 copies as compared to 2 copies) as well as a nucleotide sequence variation in EGFR (e.g., K467I) are detected indicating that the subject has developed resistance to cetuximab. Cetuximab treatment is ceased and the patient is started on a therapy other than anti-EGFR therapy (e.g., standard of care chemotherapy).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a cancer in a subject, the method comprising administering to the subject a cancer treatment other than an anti-EGFR therapy, wherein the cancer comprises cancer cells, the cancer cells comprising an EGFR nucleotide sequence variant that encodes EGFR comprising a T130A variation.

2. The method of claim 1, wherein the cancer has been determined to comprise cancer cells comprising the EGFR nucleotide sequence variant.

3. The method of claim 1, wherein the cancer is colorectal cancer or head and neck cancer.

4. The method of claim 1, wherein the subject has previously been treated with anti-EGFR therapy.

5. The method of claim 1, wherein the cancer comprises cancer cells comprising an EGFR gene amplification.

6. The method of claim 1, wherein the cancer is unresponsive to cetuximab.

7. The method of claim 1, wherein the subject is refractory to 5-FU-based therapy.

8. The method of claim 1, wherein the cancer cells further comprise a KRAS nucleotide sequence variant and/or a KRAS gene amplification.

9. The method of claim 1, wherein the cancer cells further comprise a KRAS nucleotide sequence variant that encodes a G12C, G12R, G13D, or Q61H KRAS variant.

10. The method of claim 1, wherein the cancer cells do not comprise a KRAS nucleotide sequence variant.

11. The method of claim 1, wherein the cancer has been determined not to comprise cancer cells that comprise a KRAS nucleotide sequence variant.

12. The method of claim 1, wherein the cancer has been determined not to comprise cancer cells that comprise a KRAS nucleotide sequence variant that encodes a G12C, G12R, G13D, or Q61H KRAS variant.

13. A method comprising:
(a) in a subject having a cancer, determining that the cancer comprises cancer cells having at least one EGFR nucleotide sequence variant encoding an EGFR comprising a T130A-EGFR variation by obtaining sequence data from a sample comprising cell free DNA, a tumor sample, or a blood sample and
(b) commencing a therapy, wherein (i) the therapy is other than anti-EGFR therapy, or (ii) the subject was treated with a previous therapy, the previous therapy was an anti-EGFR therapy, and the commenced therapy is an alternative therapy which optionally comprises an EGFR tyrosine kinase inhibitor, an anti-EGFR therapy different from the previous anti-EGFR therapy, or a therapy other than anti-EGFR therapy.

14. The method of claim 13, wherein the cancer is colorectal cancer or head and neck cancer.

15. The method of claim 13, wherein the determining comprises:
(a) in a sample comprising nucleic acids from a cancer cell of a subject, selectively enriching for one or more nucleic acids comprising EGFR nucleotide sequences, to produce an enriched sample;
(b) sequencing the one or more nucleic acids comprising EGFR nucleotide sequences from the enriched sample to produce sequence reads; and
(c) determining, among the sequence reads, a presence of the at least one EGFR nucleotide sequence variant.

16. The method of claim 15, wherein the selective enrichment comprises sequence capture of polynucleotides containing the at least one EGFR nucleotide sequence variant.

17. The method of claim 13, wherein the therapy is other than anti-EGFR therapy.

* * * * *